United States Patent
Froehlich (10) Patent No.: US 8,052,754 B2
(45) Date of Patent: Nov. 8, 2011

(54) INTERVERTEBRAL ENDOPROSTHESIS

(75) Inventor: Markus Froehlich, Balterswil (CH)

(73) Assignee: Zimmer GmbH, Winterthur (CH)

(*) Notice: Subject to any disclaimer, the term of this patent is extended or adjusted under 35 U.S.C. 154(b) by 994 days.

(21) Appl. No.: 11/863,884

(22) Filed: Sep. 28, 2007

(65) Prior Publication Data

US 2009/0088850 A1   Apr. 2, 2009

(51) Int. Cl.
*A61F 2/44* (2006.01)
(52) U.S. Cl. .................. 623/17.16; 623/17.15
(58) Field of Classification Search ............... 623/17.11, 623/17.12, 17.14, 17.13, 17.15, 17.16
See application file for complete search history.

(56) References Cited

U.S. PATENT DOCUMENTS

| | | | | |
|---|---|---|---|---|
| 4,261,063 A * | 4/1981 | Blanquaert | ................. | 623/23.46 |
| 4,997,432 A | 3/1991 | Keller | | |
| 5,674,294 A * | 10/1997 | Bainville et al. | ............ | 623/17.16 |
| 5,807,407 A * | 9/1998 | England et al. | ................ | 128/898 |
| 5,895,428 A | 4/1999 | Berry | | |
| 5,989,291 A | 11/1999 | Ralph et al. | | |
| 6,156,067 A | 12/2000 | Bryan et al. | | |
| 6,187,043 B1 | 2/2001 | Ledergerber | | |
| 6,682,562 B2 * | 1/2004 | Viart et al. | ................. | 623/17.14 |
| 6,966,931 B2 | 11/2005 | Huang | | |
| 7,025,787 B2 | 4/2006 | Bryan et al. | | |
| 7,101,399 B2 | 9/2006 | Errico et al. | | |
| 7,115,144 B2 | 10/2006 | Diaz et al. | | |
| 7,122,055 B2 | 10/2006 | Ralph et al. | | |
| 7,141,069 B2 | 11/2006 | Errico et al. | | |
| 2002/0035400 A1 | 3/2002 | Bryan et al. | | |
| 2002/0128654 A1 * | 9/2002 | Steger et al. | .................... | 606/69 |
| 2002/0128715 A1 | 9/2002 | Bryan et al. | | |
| 2003/0065330 A1 * | 4/2003 | Zucherman et al. | ............ | 606/61 |
| 2003/0191534 A1 * | 10/2003 | Viart et al. | ................. | 623/17.15 |
| 2004/0054411 A1 * | 3/2004 | Kelly et al. | ................ | 623/17.13 |
| 2005/0228500 A1 | 10/2005 | Kim et al. | | |
| 2005/0251260 A1 | 11/2005 | Gerber et al. | | |
| 2005/0261772 A1 * | 11/2005 | Filippi et al. | ................ | 623/17.13 |
| 2006/0036325 A1 | 2/2006 | Paul et al. | | |
| 2006/0041313 A1 * | 2/2006 | Allard et al. | ................ | 623/17.15 |
| 2006/0142862 A1 * | 6/2006 | Diaz et al. | .................. | 623/17.13 |
| 2006/0235523 A1 | 10/2006 | Gil | | |
| 2006/0235524 A1 | 10/2006 | Petit et al. | | |
| 2006/0235535 A1 | 10/2006 | Ferree et al. | | |
| 2006/0276900 A1 | 12/2006 | Carpenter | | |

FOREIGN PATENT DOCUMENTS

| | | |
|---|---|---|
| CA | 2614993 A1 | 9/2005 |
| FR | 2851157 A1 | 2/2003 |

(Continued)

*Primary Examiner* — Thomas C. Barrett
*Assistant Examiner* — Christian Sevilla
(74) *Attorney, Agent, or Firm* — Seager Tufte Wickhem LLC (57) ABSTRACT

An intervertebral endoprosthesis for insertion into the intervertebral space between two adjacent vertebrae is provided that includes first and second base members, each having a first surface configured to engage one of the vertebrae and a second opposite surface and a resilient insert disposed between the base members. The insert includes an outer shell defining an interior chamber and is disposed in contacting engagement with the second surface of each of the base members. The resilient insert further includes a core disposed within the chamber and connected to the outer shell. The intervertebral endoprosthesis further includes first and second coupling members, each of the coupling members extending between the core of the resilient insert and one of the base members. The first and second coupling members independently couple the first and second base members to the resilient insert, wherein the first and second base members are movable independently of one another and the adjacent vertebrae are movable independently of one another when the intervertebral endoprosthesis is inserted into the disc space.

24 Claims, 4 Drawing Sheets

FOREIGN PATENT DOCUMENTS

| | | |
|---|---|---|
| WO | 2004016217 A2 | 2/2004 |
| WO | 2005006944 A2 | 1/2005 |
| WO | 2005011522 A2 | 2/2005 |
| WO | 2005034864 A2 | 4/2005 |
| WO | 2006004848 A1 | 1/2006 |
| WO | 2008100574 A2 | 8/2008 |

* cited by examiner

INTERVERTEBRAL ENDOPROSTHESIS

FIELD OF THE INVENTION

The present invention relates generally to endoprostheses, and more particularly, to intervertebral endoprostheses.

BACKGROUND OF THE INVENTION

Various conditions, such as degenerative diseases, may result in the herniation of a spinal disc. This can often result in debilitating symptoms, including intractable pain, weakness, sensory loss, and incontinence. If conservative treatment of this condition is not successful, a surgical procedure known as a discectomy may be performed wherein at least a portion of the herniated disc is removed. In some instances, another surgical procedure may be performed to fuse together the two vertebrae adjacent the affected disc space. This is accomplished by removing the cartilaginous base members of the adjacent vertebrae and inserting a bone graft or other endoprosthesis between the two vertebrae.

In an attempt to provide more flexibility at the affected disc space, various intervertebral endoprostheses have been developed that include a pair of base members and a center body, or core, which may be resilient or made of metal, disposed between the base members. When inserted into the affected intervertebral disc space, each base member is placed in contacting engagement with one of the adjacent vertebrae. Known intervertebral endoprostheses of this type may be subject to one or more of the following disadvantages, depending upon the particular configuration of the prostheses: inadequate compliancy and failure to replicate the non-linear force versus displacement and damping characteristics of a natural disc; failure to permit the full range-of-motion that is available with a natural disc or insufficient stability (unconstrained); and undesirable wear on surfaces that slide relative to one another.

In view of the foregoing, it may be appreciated that there is a need for improved intervertebral endoprostheses as an alternative to bone fusion grafts and other known intervertebral endoprostheses.

SUMMARY OF THE INVENTION

While the invention will be described in connection with certain embodiments, it will be understood that the invention is not limited to these embodiments. On the contrary, the invention includes all alternatives, modifications and equivalents as may be included within the spirit and scope of the present invention.

An intervertebral endoprosthesis is provided for insertion into the intervertebral space between two adjacent vertebrae. The intervertebral endoprosthesis includes first and second base members, each having a first surface configured to engage one of the vertebrae and a second opposite surface, and a resilient insert disposed between the base members. The insert includes an outer shell defining an interior chamber, with the outer shell disposed in contacting engagement with the second surface of each of the first and second base members. The resilient insert further includes a core disposed within the chamber and connected to the outer shell. The intervertebral endoprosthesis further includes first and second coupling members, each extending between the core and one of the base members. The first and second coupling members independently couple the first and second base members, respectively, to the resilient insert, wherein the first and second base members are movable independently of one another and the adjacent vertebrae are movable independently of one another when the intervertebral endoprosthesis is inserted into the disc space.

In other embodiments, the intervertebral endoprosthesis may include one or more of the following features. The first and second coupling members may have a head disposed within the chamber and in contacting engagement with the core and a stem extending from the head to one of the base members. The core of the resilient insert has an outer surface, that may be spherical, and the head of each coupling member may include a generally cup-shaped recess that cooperates with the outer surface of the core to permit freedom-of-motion of a respective one of the coupling members in all directions. In another exemplary embodiment, the head of each coupling member has a flat proximal surface in contacting engagement with the outer surface of the core.

The resilient insert may include a plurality of spaced struts that connect the core to the outer shell. The resilient insert may further include a plurality of apertures extending through the outer shell and communicating with the interior chamber, with each of the apertures of the resilient insert having a first inside diameter. Each of the base members may have an aperture formed therein and extending through the second surface of the respective base member which faces the resilient insert. Each of the apertures of the base members has a second inside diameter and the stem of each coupling member may extend through one of the apertures of the resilient insert and into the aperture of the respective one of the base members. The stem of each base member may be cylindrical and have an outside diameter. The outside diameter of the stem and the inside diameter of the aperture of the corresponding base member may be sized so that each of the stems engage the respective base member in a press fit.

The intervertebral endoprosthesis may be made of a metal, such as titanium, for example. Alternatively, the endoprosthesis may be made of a metallic alloy such as cobalt chromium, for example. The base members may further include a coating of vacuum plasma spray titanium on at least a portion of the surface configured to engage the respective vertebrae. The resilient insert may be made of a polymer, such as polycarbonate urethane or silicone, for example.

Each of the base members may further include at least one protrusion extending from the surface configured to engage the adjacent vertebrae. The base members may include a peripheral surface and a threaded, instrument-receiving hole formed therein and extending through the peripheral surface. The base members may also include a plurality of non-threaded holes formed therein and extending through the peripheral surface, with the threaded hole being disposed intermediate of first and second ones of the non-threaded holes. The resilient insert may include an annular ring extending between and integral with first and second convex portions.

According to another aspect of the present invention, a method of manufacturing an intervertebral endoprosthesis is provided that approximates the mechanical properties of a natural intervertebral disc disposed between two adjacent vertebrae and that permits approximately the same freedom-of-motion of the vertebrae, in all directions, as that permitted by the natural intervertebral disc, when the intervertebral endoprosthesis is inserted between the adjacent vertebrae after excision of the natural disc. The method includes the steps of providing first and second base members and a resilient insert disposed between the base members. The method further includes forming the resilient insert to include an outer shell defining an interior chamber and a core disposed within the chamber and connected to the outer shell. The method also includes using a pair of coupling members to independently couple the base members to the resilient insert that includes placing a proximal portion of each of the coupling members in contacting engagement with the core and configuring a distal portion of each of the coupling members to extend between the corresponding proximal portion and one of the base members.

In other embodiments, the method may further include one or more of the following steps. The core may be formed to have a spherical outer surface and a recess may be created in the proximal portion of each coupling member, with the recess being generally cup-shaped, and with the recess cooperating with the outer surface of the core to permit freedom-of-motion of the coupling member in all directions. The core may be made of polycarbonate urethane and the base members may be made of cobalt chromium.

BRIEF DESCRIPTION OF THE DRAWINGS

The accompanying drawings, which are incorporated in and constitute a part of this specification, illustrate embodiments of the invention and, together with a general description of the invention given above, and a detailed description of the embodiments given below, serve to explain the principles of the invention.

DETAILED DESCRIPTION OF THE PREFERRED EMBODIMENT

Figure 1:
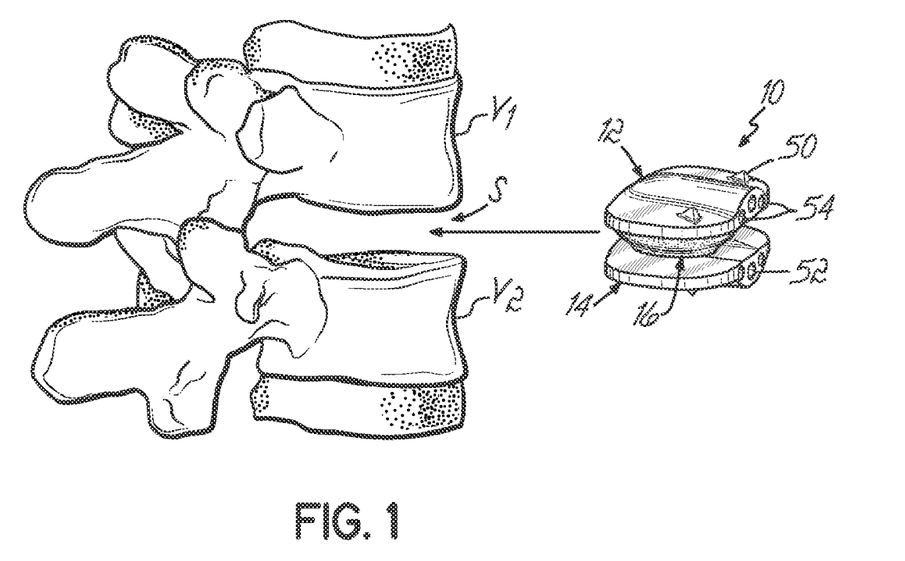
FIG. 1 is a perspective view illustrating two adjacent vertebrae and an intervertebral endoprosthesis according to one embodiment of the present invention, prior to insertion into the intervertebral disc space between the vertebrae.
Figure 2:
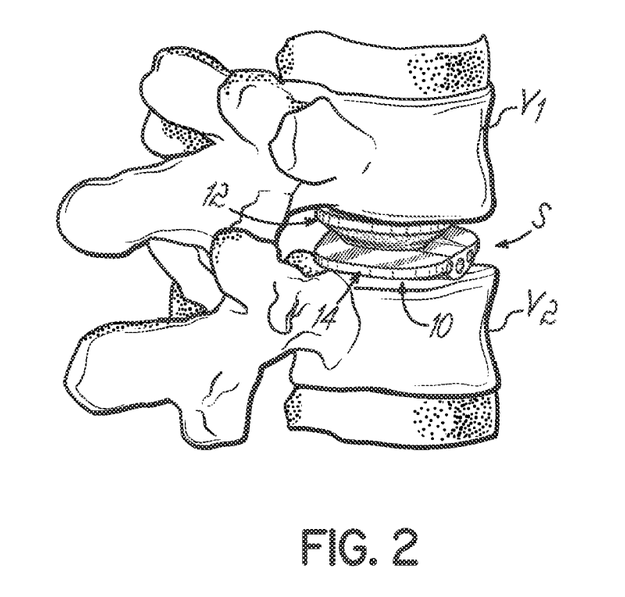
FIG. 2 is a perspective view similar to FIG. 1, but with the intervertebral endoprosthesis shown in FIG. 1, inserted into the disc space.

FIG. 1 illustrates an intervertebral endoprosthesis 10 according to one embodiment of the present invention, in the process of being inserted into a disc space S between two adjacent vertebrae V1 and V2. The disc space S may be created by a discectomy procedure as well as removal of a portion of the cartilaginous base members of vertebrae V1 and V2. FIG. 2 illustrates the intervertebral endoprosthesis 10 inserted into disc space S between vertebrae V1 and V2.

With further reference to FIGS. 3-6, the intervertebral endoprosthesis 10 includes a first base member 12, a second base member 14 and a resilient insert 16 disposed between base members 12 and 14. Endoprosthesis 10 further includes two separate coupling members 18a, 18b that independently couple the respective base members 12, 14 to the resilient insert 16. Accordingly, coupling member 18a and base member 12 may move independently from the movement of coupling member 18b and base member 14. In the illustrative embodiment shown in FIGS. 1-6, the coupling members 18a and 18b are identical.

Base member 12 includes a first surface 30 configured to engage a vertebrae, such as vertebrae V1, and a second, opposite surface 32 that faces and engages the resilient insert 16. Base member 12 further includes a peripheral surface 34 that extends around base member 12 and between surfaces 30 and 32. Similarly, base member 14 includes a first surface 40 configured to engage a vertebrae, such as vertebrae V2, and a second, opposite surface 42 that faces and engages the resilient insert 16. Base member 14 further includes a peripheral surface 44 that extends around base member 14 and between surfaces 40 and 42. Base members 12 and 14 may include a plurality of protrusions 50 extending from surfaces 30 and 40 respectively, to engage vertebrae such as vertebrae V1 and V2 to prevent, or at least inhibit, movement of base members 12, 14 relative to vertebrae V1, V2 respectively. The particular number and configuration of protrusions 50 may vary with application.

Figures 5, 6:
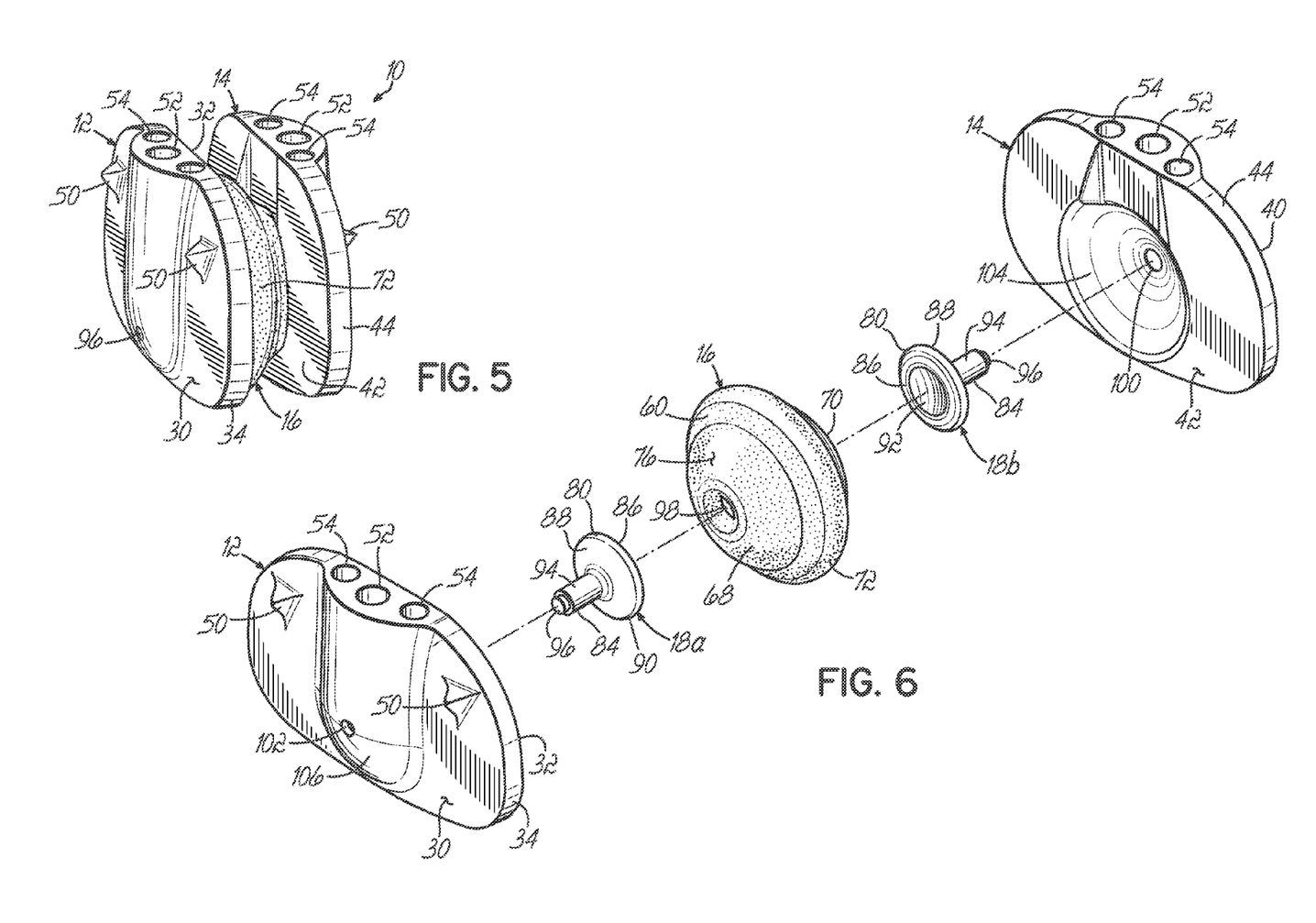
FIG. 5 is another perspective view of the intervertebral endoprosthesis shown in FIGS. 1-4.
FIG. 6 is an exploded assembly view, in perspective, further illustrating the intervertebral endoprosthesis shown in FIGS. 1-5.

Base members 12 and 14 may further include at least one threaded hole 52 that is suitable for receiving a mating threaded stud or bolt of an insertion tool (not shown) to facilitate insertion of the intervertebral endoprosthesis 10 into disc space S. In this regard, base members 12 and 14 may also include a plurality of non-threaded holes 54, for example, one on either side of threaded hole 52, that are suitable to accept pins that may be formed on the insertion tool to prevent base members 12 and 14 from rotating during the insertion process. Holes 52 and 54 are formed in the peripheral surfaces 34 and 44 of base members 12 and 14, respectively. In the illustrative embodiment, holes 52, 54 are formed in an anterior portion of peripheral surfaces 34, 44 to accommodate an anterior surgical approach to insert intervertebral endoprosthesis 10 into disc space S. However, holes 52, 54 may be positioned in other portions of surfaces 34, 44 if different surgical approaches are used.

Base members 12 and 14 may be made of a metallic alloy or a metal. Examples of suitable materials include, but are not limited to, cobalt chromium and titanium. If a material such as cobalt chromium is used, the vertebral-engaging surfaces 30 and 40 of base members 12 and 14, respectively, may include a vacuum plasma spray coating of titanium, or other suitable biocompatible coating, deposited thereon for wear protection. Coupling members 18a, 18b may be made of the same material as base members 12, 14.

Figure 3:
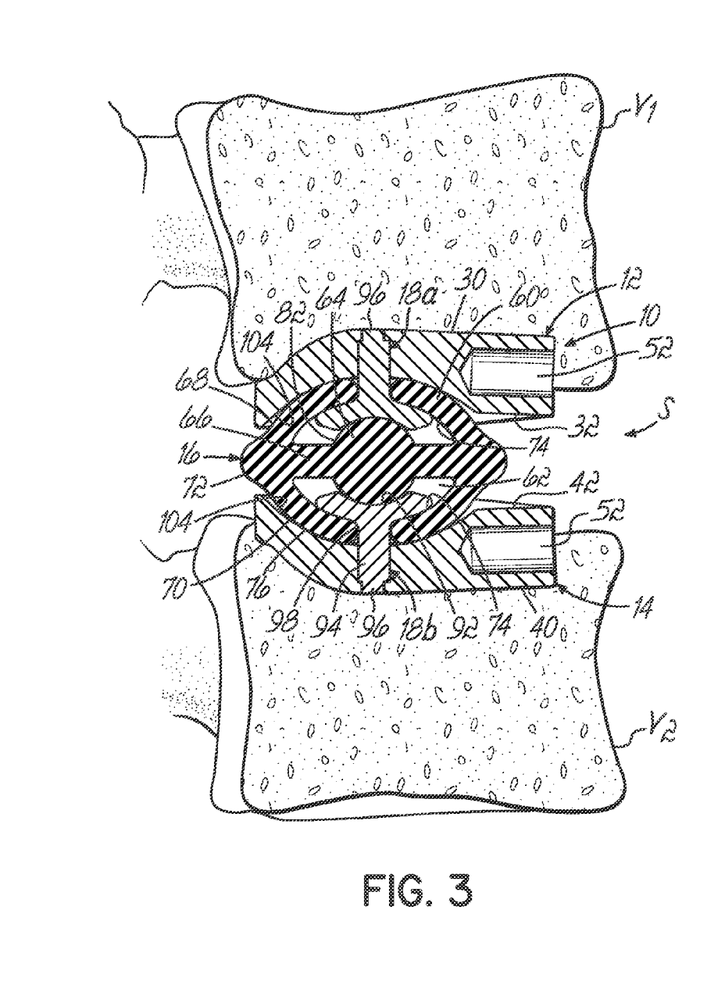
FIG. 3 is a cross-sectional view further illustrating the intervertebral endoprosthesis shown in FIGS. 1 and 2, with the endoprosthesis shown in a neutral position, i.e., without deformation, between the adjacent vertebrae.
Figure 4:
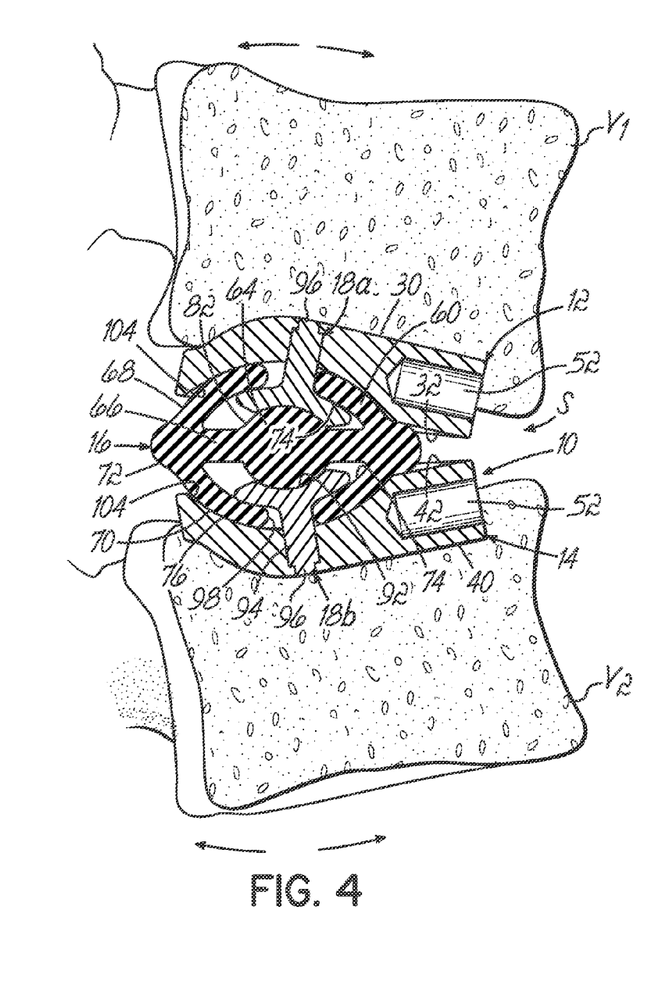
FIG. 4 is a cross-sectional view similar to FIG. 3 but with the intervertebral endoprosthesis partially compressed due to the movement of the adjacent vertebrae.

The resilient insert 16 includes an outer shell 60 defining an interior chamber 62 and a core 64 disposed within chamber 62. Core 64 may be connected to outer shell 60 by a plurality of spaced struts 66. The outer shell 60 is disposed in contacting engagement with base members 12 and 14. More particularly, outer shell 60 is disposed in contacting engagement with surfaces 32 and 42 of base members 12 and 14, respectively. In the illustrative embodiment, outer shell 60 includes first 68 and second 70 convex portions and an annular ring 72 extending between and integral with convex portions 68, 70 that contact base members 12, 14 respectively. Outer shell 60 further includes inner 74 and outer 76 surfaces. Insert 16 may be made of a polymer having adequate resiliency. Examples of suitable polymers that may be used include, but are not limited to, polycarbonate urethane and silicone.

Referring to FIGS. 3, 4 and 6, each of the coupling members 18a, 18b extends between the core 64 and a respective one of base members 12, 14. Each coupling member 18a, 18b includes a proximal portion (i.e., portion closest to core 64), or head 80, disposed within interior chamber 62 and in contacting engagement with an outer surface 82 of core 64. Each coupling member 18a, 18b also includes a distal portion, or stem, 84 that extends from proximal portion 80 through outer shell 60 to a respective one of the base members 12, 14 as subsequently described further. In one embodiment, the proximal portion 80 of coupling members 18a, 18b and interior chamber 62 can be round. In another embodiment, the proximal portion 80 and interior chamber 62 can have an oval shape to restrict torsional rotation of the implant. The proximal portion 80 of coupling members 18a, 18b has proximal 86 and distal 88 surfaces and a peripheral surface 90 extending between and integral with proximal 86 and distal 88 surfaces. The proximal surface 86 defines a generally cup-shaped recess 92 that cooperates with outer surface 82 of core 64 to permit freedom-of-motion of coupling members 18a, 18b in all directions.

The distal portion 84 of each coupling member 18a, 18b includes a stem 94 that may be cylindrical, with an outside diameter $d_1$. Distal portion 84 may further include a protrusion 96, that may also be cylindrical, extending from stem 94. The stem 94 of each coupling member 18a, 18b extends from proximal portion 80 through outer shell 60 to the respective base member 12, 14. The outer shell 60 of resilient insert 16 includes a pair of apertures 98 formed therein, each having an inside diameter $d_2$. Each base member 12, 14 includes an aperture 100 formed therein to receive the stem 94 of the corresponding coupling member 18a, 18b. Each aperture 100 has an inside diameter $d_3$. As shown in FIGS. 3 and 4, the stems 94 of coupling members 18a, 18b extend through the corresponding aperture 98 of outer shell 60 and into the aperture 100 of the corresponding one of base members 12, 14. The inside diameter $d_2$ of apertures 98 may be sized so that it is only slightly larger than the outside diameter $d_1$ of stem 94, or alternatively $d_2$ may be sized so that it is significantly larger than $d_1$. The inside diameter $d_3$ of apertures 100 in base members 12, 14 may be sized so that stems 94 engage base members 12, 14 in a press fit thereby securing each stem 94 to the respective base member 12, 14. The protrusion 96 of each coupling member 18a, 18b may be disposed within an aperture 102 formed in the respective base member 12, 14 and may be welded to the respective base member.

Surfaces 32 and 42 of base members 12, 14, respectively, may each define a concave recess 104 that engages the respective convex portions 68, 70 of shell 60. The incorporation of recesses 104 permits the resilient insert 16 to be larger for a given size of disc space S and provides more material to be deformed in use, which may be desirable. The radius of curvature of each recess 104 may be greater than the radius of curvature of convex portions 68, 70 so that the outer surface 76 of shell 60 is not congruent with the surfaces 32 and 42 in the area of recesses 104 in a neutral or no load condition. This may be desirable to avoid overloading insert 16 in maximum deflection conditions. Base members 12, 14 may further include a bulged portion 106 defined by surfaces 30, 40 of base members 12, 14 respectively. The bulged portions 106 may engage surgically created recesses, having complementary shapes, formed in vertebrae V1 and V2.

When inserted into disc space S, the intervertebral endoprosthesis 10 approximates the mechanical properties of the natural disc removed from space S, including the damping characteristics and non-linear force versus deflection characteristics of the natural disc. Since base members 12 and 14 may move independently from one another, and are secured to vertebrae V1 and V2, respectively, vertebrae V1 and V2 may move independently from one another. Therefore, the intervertebral endoprosthesis 10 also permits approximately the same range-of-motion, in all directions, of vertebrae V1 and V2 as that permitted by the natural disc removed from disc space S. These characteristics of intervertebral endoprosthesis 10 are achieved by the material and configuration of resilient insert 16, as well as the relationship among insert 16, coupling members 18a, 18b and base members 12, 14 including the fact that base members 12 and 14 are independently coupled to insert 16 via separate coupling members 18a and 18b.

Figure 7:
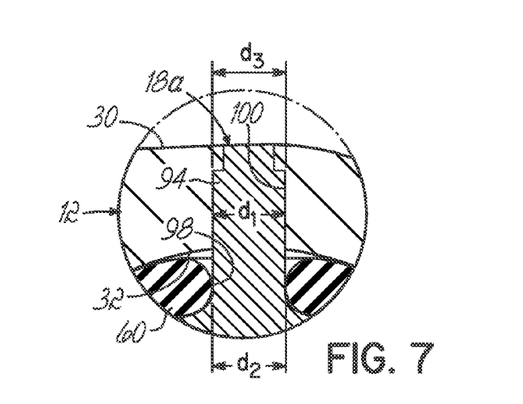
FIG. 7 is an enlarged fragmentary view further illustrating a portion of the intervertebral endoprosthesis shown in FIG. 3.
Figure 8:
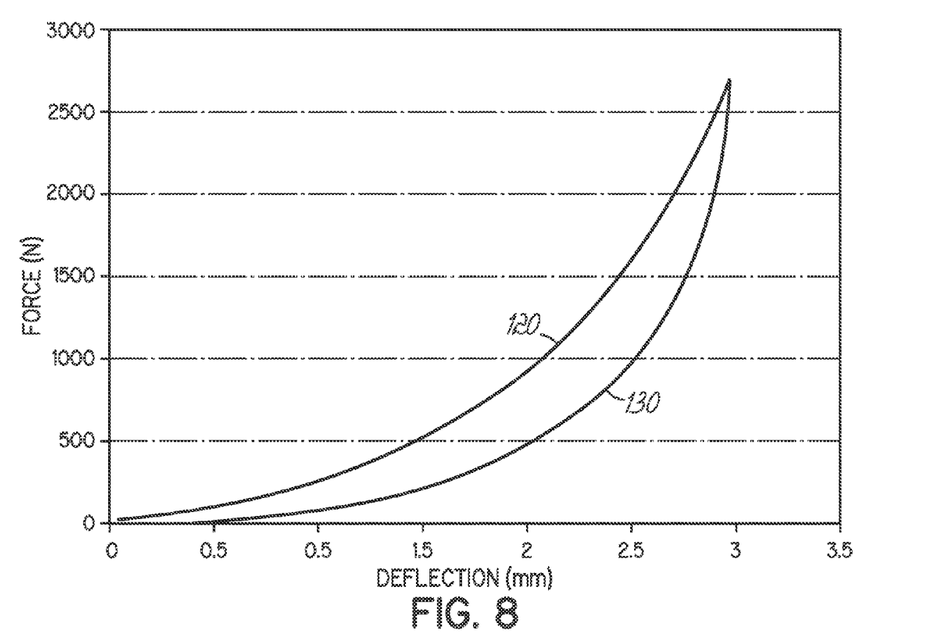
FIG. 8 is a graph illustrating two load versus deflection curves.

As the compression of resilient insert 16 increases, as a result of various loading conditions, an increasing amount of the outer surface 76 of outer shell 60 of the resilient insert 16 comes into contacting engagement with the surfaces 32 and 42 of base members 12, 14. For example, the outer surface 76 of shell 60 may become congruent with surfaces 32 and 42 in the area of recesses 104. Additional areas of outer surface 76 may also contact surfaces 32 and 42. For example, if resilient insert 16 is sufficiently compressed, the outer surface 76 in the area of the annular portion, or ring 72, of outer shell 60 may also contact surfaces 32 and 42. As a result of the foregoing, the force versus deflection characteristic of intervertebral endoprosthesis 10 is non-linear and approximates that of a natural disc. This non-linear response is illustrated in FIG. 7 which includes a first 120 and second 130 non-linear load versus deflection curves. Curve 120 was created by loading a prototype intervertebral endoprosthesis having the configuration of intervertebral endoprosthesis 10, and measuring the force resulting from various deflections of the prototype. Curve 130 was created by unloading the prototype and again measuring the force resulting from various deflections of the prototype during the unloading process. The difference between curves 120 and 130, i.e., the difference in force for a given deflection, is evidence of the damping characteristics of the prototype intervertebral endoprosthesis, and hence intervertebral endoprosthesis 10, with the magnitude of damping being a function of the area between these curves.

The magnitude of the motion of vertebrae V1 and V2, in all directions, may be selected as a function of: the material properties of resilient insert 16; the relationship between the outside diameter $d_1$ of stems 94 of coupling members 18a, 18b and the inside diameter $d_2$ of apertures 98 in outer shell 60 of resilient insert 16; and the relative size and shape of the proximal portion 80 of coupling members 18a, 18b as compared to the size of interior chamber 62 of resilient insert 16. If the inside diameter $d_2$ of apertures 98 is approximately the same as the outside diameter $d_1$ of stems 94, the stems 94 deform resilient insert 16 as base members 12, 14 and vertebrae V1 and V2 move relative to insert 16. As may be appreciated, this movement may be controlled by the material properties of insert 16. If $d_2$ is significantly greater than $d_1$, then the motion of base members 12, 14 and vertebrae V1, V2 may be stopped when the proximal portions 80 of coupling members 18a, 18b contact the inner surface 74 or struts 66 of shell 60 of insert 16 or when stems 94 contact the edges of insert 16 defining apertures 98, or a combination of the above. In each case, some deformation of insert 16 may occur.

Figure 9:
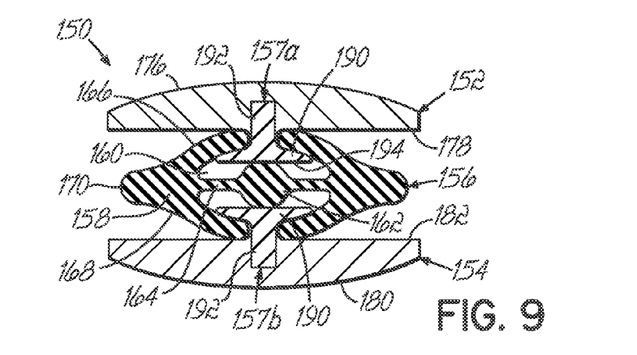
FIG. 9 is a cross-sectional view similar to FIG. 3 illustrating an intervertebral endoprosthesis according to another embodiment of the present invention.

FIG. 9 illustrates an intervertebral endoprosthesis 150 according to another embodiment of the present invention. The intervertebral endoprosthesis 150 includes base members 152 and 154, a resilient insert 156 disposed between base members 152, 154 and two separate coupling members 157a and 157b that independently couple the respective base member 152, 154 to the resilient insert 156. Accordingly, coupling member 157a and base member 152 may move independently from the movement of coupling member 157b and base member 154. In the embodiment illustrated in FIG. 9, coupling members 157a, 157b are separate from one another and separate from base members 152, 154. In another embodiment, coupling members 157a, 157b may be integrally formed with base members 152, 154 respectively. Resilient insert 156 may be made of the same materials as resilient insert 16 and has substantially the same configuration as insert 16, but may have a smaller height than insert 16 since base members 152, 154 do not include a recess, such as recess 104, formed therein. Similar to insert 16, insert 156 includes an outer shell 158 that defines an interior chamber 160 and also includes a core 162 disposed within chamber 160. The core 162 may be interconnected to outer shell 158 by a plurality of spaced struts 164. Like outer shell 60 of insert 16, outer shell 158 includes a first convex portion 166 contacting base member 152, a second convex portion 168 contacting base member 154 and an annular portion, or ring, 170 extending between and integral with convex portions 166, 168. As seen by comparing FIG. 9 to FIG. 3, the annular portion 170 of insert 156 may be more pronounced, or elongated, than the annular portion 72 of insert 16.

Base member 152 includes a first vertebral-engaging surface 176 and a second, opposite surface 178 facing and engaging insert 156. Similarly, base member 154 includes a first, vertebral-engaging surface 180 and a second, opposite face 182 facing and engaging insert 156. As shown in FIG. 9, surfaces 178 and 182 do not define recesses but instead are substantially flat. Unlike base members 12, 14, base members 152, 154 do not include a bulging portion like bulging portion 106, that engages adjacent vertebrae. Base members 152, 154 may include a plurality of protrusions (not shown) such as protrusions 50 of insert 16, that extend from surfaces 176 and 180 and engage the adjacent vertebrae.

Referring to FIG. 9, each of the coupling members 157a, 157b extends between core 162 and a respective one of base members 152, 154. Each coupling member 157a, 157b includes a proximal portion (i.e., closest to core 162), or head 190, disposed within interior chamber 160, and a distal portion 192, which may be a cylindrical stem. A proximal surface 194 of proximal portion 190 is in contacting engagement with core 162. As shown in FIG. 9, the proximal surfaces 194 are not arcuate, but instead are substantially flat. The distal portion or stem 192 extends from proximal portion or head 190 through outer shell 158 to a respective one of base members 152, 154. The outer shell 158 includes apertures formed therein and base members 152, 154 include mating apertures, to receive the stems 192 of coupling members 157a and 157b. The apertures in base members 152, 154 may be sized so that the distal portions 192 engage the respective base member 152, 154 in a press fit, thereby securing each stem 192 to the respective base member 152, 154. Stems 192 may also be welded, or otherwise bonded, to the respective base member 152, 154, for example through access holes (not shown) extending through surfaces 176, 180.

Similar to intervertebral endoprosthesis 10, as a compressive force applied to base members 152, 154 and insert 156 increases, the contact area increases between the outside surface of shell 158 and surfaces 178, 180 of base members 152, 154, respectively. Like intervertebral endoprosthesis 10, intervertebral endoprosthesis 150 approximates the mechanical properties of a natural disc disposed between two adjacent vertebrae. Since base members 152 and 154 may move independently from one another, and are engaged with adjacent vertebrae, the adjacent vertebrae may move independently from one another. Therefore, the intervertebral endoprosthesis 150 also permits approximately the same range-of-motion, in all directions, of the vertebrae as that permitted by the natural disc, when intervertebral endoprosthesis 150 is inserted in the disc space between the two vertebrae after removal of the natural disc.

While the present invention has been illustrated by the description of and exemplary embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. An intervertebral endoprosthesis for insertion into the intervertebral space between two adjacent vertebrae, said intervertebral endoprosthesis comprising:
   first and second base members, each having a first surface configured to engage one of the vertebrae and a second opposite surface;
   a resilient insert disposed between said base members, said insert comprising an outer shell defining an interior chamber, said outer shell disposed in contacting engagement with said second surface of each of said first and second base members, said resilient insert further including a core disposed within said chamber, said core being integral with said outer shell;
   first and second coupling members, each of said coupling members extending between said core and one of said base members, said first and second coupling members independently coupling said first and second base members, respectively, to said resilient insert, wherein said first and second base members are movable independently of one another and the adjacent vertebrae are movable independently of one another when the intervertebral endoprosthesis is inserted into the disc space;
   wherein said resilient insert is a monolithic insert; and
   wherein said resilient insert and each of said base members are slidable relative to each other in any direction along a spherical surface.

2. The intervertebral endoprosthesis of claim 1, wherein:
   each of said first and second coupling members has a proximal portion disposed within said chamber and in contacting engagement with said core and a distal portion extending therefrom to one of said base members.

3. The intervertebral endoprosthesis of claim 2, wherein:
   said proximal portion of each of said coupling members comprises a proximal surface defining a generally cup-shaped recess that cooperates with said outer surface of said core to permit freedom-of-motion of a respective one of said coupling members in all directions.

4. The intervertebral endoprosthesis of claim 1, wherein:
   said base members are made of cobalt chromium and said resilient insert is made of polycarbonate urethane.

5. The intervertebral endoprosthesis of claim 1, wherein:
   said resilient insert further includes a plurality of spaced struts, said struts connecting said core to said outer shell.

6. An intervertebral endoprosthesis for insertion into the intervertebral space between two adjacent vertebrae, said intervertebral endoprosthesis comprising:
   first and second base members, each having a first surface configured to engage one of the vertebrae and a second opposite surface;

a unitary resilient insert disposed between said base members, said insert comprising an outer shell defining an interior chamber, said outer shell disposed in contacting engagement with said second surface of each of said first and second base members, said resilient insert further including a core disposed within said chamber and connected to said outer shell, wherein said core is spaced apart from said outer shell;

first and second coupling members, each having a head disposed within said chamber and in contacting engagement with said core and a stem extending from said head to one of said base members, said first and second coupling members independently coupling said first and second base members, respectively, to said resilient insert, wherein said first and second base members are movable independently of one another and the adjacent vertebrae are movable independently of one another when the intervertebral endoprosthesis is inserted into said disc space wherein said unitary resilient insert is a monolithic insert; and wherein said unitary resilient insert and each of said base members are slidable relative to each other in any direction along a spherical surface.

7. The intervertebral endoprosthesis of claim 6, wherein:
said core of said resilient insert has an outer surface;
said head of each of said coupling members includes a proximal surface that defines a generally cup-shaped recess that cooperates with said outer surface of said core to permit freedom-of-motion of a respective one of said coupling members in all directions.

8. The intervertebral endoprosthesis of claim 6, wherein:
said resilient insert further includes a plurality of spaced struts, said struts connecting said core to said outer shell.

9. The intervertebral endoprosthesis of claim 6, wherein:
said resilient insert further comprises a plurality of apertures extending through said outer shell and communicating with said interior chamber, each of said apertures of said resilient insert having a first inside diameter;
each of said base members has an aperture formed therein and extending through said second surface which faces said resilient insert, each of said apertures of said base members having a second inside diameter;
said stem of each of said coupling members extends through one of said apertures of said resilient insert and into said aperture of the respective one of said base members.

10. The intervertebral endoprosthesis of claim 9, wherein:
said stem is cylindrical and has an outside diameter;
said outside diameter of said stem and said second inside diameter of said aperture of said base member are sized so that each of said stems engage the respective base member in a press fit.

11. The intervertebral endoprosthesis of claim 6, wherein:
said base members are made of a material selected from the group consisting of a metal and a metallic alloy.

12. The intervertebral endoprosthesis of claim 11, wherein:
said material is cobalt chromium.

13. The intervertebral endoprosthesis of claim 11, wherein:
said material is titanium.

14. The intervertebral endoprosthesis of claim 11, wherein:
said base members further comprise a coating of vacuum plasma spray titanium on at least a portion of said first surface.

15. The intervertebral endoprosthesis of claim 1, wherein:
said resilient insert is made of a polymer.

16. The intervertebral endoprosthesis of claim 6, wherein:
each of said base members further comprise at least one protrusion extending from said first surface to engage the adjacent one of the vertebrae.

17. The intervertebral endoprosthesis of claim 6, wherein:
said base members further comprise a peripheral surface, and a threaded, instrument-receiving hole formed therein and extending through said peripheral surface.

18. The intervertebral endoprosthesis of claim 17, wherein:
said base members further comprise a plurality of non-threaded holes formed therein and extending through said peripheral surface, said threaded hole being disposed intermediate of first and second ones of said non-threaded holes.

19. An intervertebral endoprosthesis of claim 6, wherein:
said second surface of each of said base members defines a recess having a concave shape;
said outer shell comprises first and second convex portions, said first convex portion engaging said recess of one of said base members, said second convex portion engaging said recess of the other one of said base members.

20. An intervertebral endoprosthesis of claim 19, wherein:
said resilient insert further comprises an annular ring extending between said first and second convex portions, said annular ring and said first and second convex portions being integral with one another.

21. A method of manufacturing an intervertebral endoprosthesis that approximates the mechanical properties of a natural intervertebral disc disposed between two adjacent vertebrae and permits approximately the same freedom-of-motion of the vertebrae, in all directions, as that permitted by the natural intervertebral disc, when the intervertebral endoprosthesis is inserted between the two adjacent vertebrae after excision of the natural disc, comprising:
providing first and second base members and a unitary resilient insert disposed between the base members;
forming said unitary resilient insert to include an outer shell defining an interior chamber and a core disposed within the chamber and connected to but spaced from the outer shell;
using a pair of coupling members to independently couple the base members to the resilient insert comprising placing a proximal portion of each of the coupling members in contacting engagement with the core and configuring a distal portion of each of the coupling members to extend between the corresponding proximal portion and one of the base members wherein said unitary resilient insert is a monolithic insert; and wherein said unitary resilient insert and each of said base members are slidable relative to each other in any direction along a spherical surface.

22. The method of claim 21, further comprising:
forming the core to have a spherical outer surface;
creating a recess in the proximal portion of each coupling member, the recess being generally cup-shaped, the recess cooperating with the outer surface of the core to permit freedom-of-motion of the coupling member in all directions.

23. The method of claim 22, further comprising:
making the core of polycarbonate urethane.

24. The method of claim 23, further comprising:
making the base members of cobalt chromium.

* * * * *